US011221107B2

(12) United States Patent
Du et al.

(10) Patent No.: US 11,221,107 B2
(45) Date of Patent: Jan. 11, 2022

(54) METHOD FOR LEAKAGE DETECTION OF UNDERGROUND PIPELINE CORRIDOR BASED ON DYNAMIC INFRARED THERMAL IMAGE PROCESSING

(71) Applicant: Yuchuan Du, Shanghai (CN)

(72) Inventors: Yuchuan Du, Shanghai (CN); Lijun Sun, Shanghai (CN); Ning Pan, Shanghai (CN); Shengchuan Jiang, Shanghai (CN); Chenglong Liu, Shanghai (CN); Jun Yan, Shanghai (CN); Qin Wang, Shanghai (CN)

(73) Assignee: Yuchuan Du, Shanghai (CN)

( * ) Notice: Subject to any disclaimer, the term of this patent is extended or adjusted under 35 U.S.C. 154(b) by 452 days.

(21) Appl. No.: 16/457,985

(22) Filed: Jun. 29, 2019

(65) Prior Publication Data

US 2019/0331301 A1    Oct. 31, 2019

Related U.S. Application Data

(63) Continuation of application No. PCT/IB2017/058540, filed on Dec. 30, 2017, and a
(Continued)

(51) Int. Cl.
*F17D 5/02* (2006.01)
*G01M 3/00* (2006.01)
(Continued)

(52) U.S. Cl.
CPC .............. *F17D 5/02* (2013.01); *E01C 23/01* (2013.01); *G01M 3/002* (2013.01);
(Continued)

(58) Field of Classification Search
CPC .......... F17D 5/02; E01C 23/01; G01M 3/002; G01M 5/0033; G01M 5/0066;
(Continued)

(56) References Cited

U.S. PATENT DOCUMENTS

| 7,073,979 | B2 * | 7/2006 | McGrew | E03F 3/06 |
| | | | | 166/298 |
| 2006/0220888 | A1 * | 10/2006 | Germouni | G06T 7/0008 |
| | | | | 340/605 |
| 2010/0025582 | A1 * | 2/2010 | Weil | G01N 25/72 |
| | | | | 250/332 |

FOREIGN PATENT DOCUMENTS

| CN | 101070947 A | 11/2007 |
| CN | 101701919 A | 5/2010 |

(Continued)

OTHER PUBLICATIONS

Starman "Automated System for Crack Detection Using Infrared Thermographic Testing" (Year: 2008).*
(Continued)

*Primary Examiner* — Regis J Betsch
*Assistant Examiner* — Kaleria Knox

(57) ABSTRACT

A method for leakage detection of underground pipeline corridor based on dynamic infrared thermal image processing. The leakage can be detected by the following steps, including: converting infrared thermal videos into infrared thermal images; obtaining the gray scale information and temperature information of internal environment of the underground pipeline corridor. The gray scale information can realize the conventional target of pipe line state identification inside the pipeline corridor, and the temperature information can be used to detect the pipe leakage.

10 Claims, 12 Drawing Sheets

Related U.S. Application Data continuation of application No. PCT/IB2016/058109, filed on Dec. 30, 2016.

(51) Int. Cl.
*E01C 23/01* (2006.01)
*G01M 5/00* (2006.01)
*G01N 21/95* (2006.01)
*G01N 33/42* (2006.01)
*G01N 21/88* (2006.01)

(52) U.S. Cl.
CPC ........ *G01M 5/0033* (2013.01); *G01M 5/0066* (2013.01); *G01N 21/95* (2013.01); *G01N 33/42* (2013.01); *G01N 2021/8845* (2013.01)

(58) Field of Classification Search
CPC .................. G01N 21/95; G01N 33/42; G01N 2012/8845; G01N 25/72; G06T 7/0008; E03F 3/06
See application file for complete search history.

(56) References Cited

FOREIGN PATENT DOCUMENTS

| | | |
|---|---|---|
| CN | 102108666 A | 6/2011 |
| CN | 102182137 A | 9/2011 |
| CN | 206573258 U | 10/2017 |
| CN | 206629279 U | 11/2017 |
| JP | H0961138 A | 3/1997 |

OTHER PUBLICATIONS

Mohd Shawal Jadin "Gas Leakage Detection Using Thermal Imaging Technique" (Year: 2014).*

* cited by examiner

METHOD FOR LEAKAGE DETECTION OF UNDERGROUND PIPELINE CORRIDOR BASED ON DYNAMIC INFRARED THERMAL IMAGE PROCESSING

CROSS-REFERENCE TO RELATED APPLICATIONS

This application is a continuation of International Application No. PCT/IB2017/058540 with a filing date of Dec. 30, 2017, designating the United States, which claims the benefit of priority from International Application No. PCT/IB2016/058109 with a filing date of Dec. 30, 2016. The content of the aforementioned applications, including any intervening amendments thereto, is incorporated herein by reference.

TECHNICAL FIELD

The present invention relates to image processing and leakage detection, and more particularly to a method for leakage detection of an underground pipeline corridor based on dynamic infrared thermal image processing. By introducing infrared thermal image, the gray scale information and temperature information of the internal environment of the underground pipe pipeline corridor can be obtained. The gray scale information can realize the conventional target of pipeline line state identification inside the pipeline corridor, and the temperature information can be used to detect the pipeline leakage and provide reference for maintenance and repair. This present invention mainly establishes a discriminant model for pipeline leakage mainly through experiments and techniques combined with machine learning.

BACKGROUND

In recent years, the construction of underground integrated pipeline corridors in China has developed rapidly, and its management and maintenance issues have become more and more prominent. Among them, leakage detection has become one of the priorities of the relevant management departments. The efficiency of traditional on-site inspection depends on the size, material, and depth of the pipeline. Besides, the inspection process requires manual intervention. The inspection conditions depend on the weather, the surface condition of the pipeline and the water pressure. The prior art for large-scale detection of leakage is still dominated by closed-circuit television monitoring technology, which is inefficient and requires manual inspection and has high time and labor costs. Thanks to the rapid development of digital image processing technology, the intelligent detection methods of underground pipeline corridor are becoming more and more diverse. The latest and most effective methods are fiber optic technology, wireless network sensor detection technology, ultrasonic guided wave technology, in-pipe micro-leakage detection technology, and thermal imaging technology.

RELATED ART

CN206573258U; CN101070947A; CN206629279U.

SUMMARY

The object of the present invention is to provide a method for leakage detection of an underground pipeline corridor based on dynamic infrared thermal image processing. The internal space of the pipeline corridor is photographed by a temperature-measuring infrared camera, and the infrared thermal image near the leakage of the pipeline is obtained. A relationship model between the leakage crack and the temperature difference between the pipeline and the leak is established, and then the machine is combined. The computer vision technology of learning establishes a discriminant model of pipeline leakage. The experimental principle is based on PCT/IB2016/058109. FIG. 1 is a technical route for identifying leaks in the interior of a pipeline corridor using an infrared thermography.

Normal images can only obtain the gray space information of the underground pipeline corridor environment space, pipeline lines and leakage cracks. The gray scale information can realize the conventional target of pipe line state identification inside the pipeline corridor. The reason why normal images are difficult to identify the leakage cracks is that the surface material of the pipe is grainy, and the gradation of gray scale often affects the identification of the crack area. We usually identify leaking cracks by identifying the width of the crack, which is determined by identifying the number of pixels in the short side of the crack area, combined with the height at which the camera position captures the crack. However, the detection method of obtaining the crack width by the identification of the crack pixel width to determine the crack severity is unreliable, because the crack width of a few millimeters may have only a few pixels in the image, and is subjected to image processing such as noise reduction. So, it is difficult to discriminate the crack only by the gray scale information of the crack acquired by the ordinary image.

Infrared temperature measurement technology uses an infrared optical system to make the infrared thermal image of the target to be measured on the infrared focal plane detector. After processing, the infrared image of the target to be measured is obtained, and then according to the gray value of the image and the calibration data, and related parameters, the temperature field distribution of the object is analyzed. The temperature measurement technology based on full-field analysis can measure the temperature of a large area, and can simultaneously obtain the temperature of multiple objects and the temperature of multiple objects, which is of great significance for analyzing the state of the object, and thus becoming a hot topic in recent years. The infrared thermal image obtained by the infrared camera can not only obtain the gray scale information of the inner space and crack of the pipeline corridor, but also obtain their temperature information, as shown in FIG. 2, which contains the gray scale information and temperature of the inner space and crack of the pipeline corridor. The temperature information can be used to detect the leakage of pipelines and provide a reference for the later maintenance and repair. The discriminant model of pipeline leakage is established mainly through experiments and computer vision technology combined with machine learning.

When detecting the leak using an infrared camera, the present invention mainly solves the following three problems.

(1) The underground pipeline corridor space is dark and damp. Using traditional methods to detect the leakage of internal pipes will be subject to various restrictions due to dim light, low temperature, and other factors, resulting in large errors. Therefore, the present invention clearly recognizes the obvious difference between the leakage area and the pipeline corridor environment through the infrared thermal image, can effectively identify the leakage point, and can display parameters such as the size of the leakage damage by using image processing technology.

(2) Leakage in underground integrated pipeline corridor is mainly divided into the leakages caused by small cracks, the leakages caused by local area damage and the leakages caused by loose pipe joint. In the above three cases, the features of the leak point are different, so the image taken by the infrared camera will show different characteristics. Therefore, the present invention needs to set a scientific infrared data information screening standard to distinguish different kinds of leakage conditions, thereby ensuring the applicability of the detection results, and providing a possibility for the targeted maintenance according to the specific classification.

(3) After successfully identifying the leakage damage in the underground integrated pipeline corridor, it is necessary to promptly extract the position information of the leakage point and feed it back to the maintenance department to facilitate the immediate repair of the dangerous leakage point in the pipeline corridor. The present invention provides an accurate and efficient positioning technology, and realizes the positioning of the leakage point by screening and matching the interest domain graphic and the template graphic.

As mentioned above, the more serious the crack development degree is, the more the temperature below the surface of the pipeline will be reflected, and the temperature below the surface of the pipeline is different from the surface temperature. Therefore, the more serious the crack development, under the same conditions, the difference between the performance and the surface temperature of the pipe will be greater. Therefore, the object of the present invention is to reflect the degree of crack development by the temperature difference between the surface of the pipe and the crack under certain conditions. Their corresponding relationship is the detection model.

The basis of the leakage analysis model with infrared thermal imaging is the temperature field information measurement function, which relies on the infrared image temperature field recognition algorithm to realize the analysis of the infrared image collected by the acquisition device or the infrared image data stored on the computer. According to the gray value of each pixel on the image, the corresponding temperature value is calculated according to a certain mathematical model, and the temperature is measured by the set temperature measurement. The temperature measurement comprises the point temperature measurement and the regional temperature measurement. The point temperature measurement is to measure the temperature of a single pixel, and the regional temperature measurement is to measure the average value of a region. Therefore, the measurement of the global, local area and point of the target scene temperature can be realized according to the image data.

At the same time, due to the different specific heat capacity of the water and water pipe materials, when the pipeline leaks, the temperature difference will occur in the vicinity of the leakage point, and the infrared camera can visually detect the temperature difference of the surface above the leaking pipe. Above-mentioned temperature measurement method realizes the perception of temperature difference.

Due to the hysteresis and accumulation of the surface temperature of the pipeline, the temperature of the pipeline surface and the interior will be different. Therefore, the dielectric material inside the pipeline will exchange heat with the pipeline surface and the ambient air through cracks or other damaged areas, while the pipeline surface and cracks are located. There will also be temperature differences. The greater the length and width of the pipe crack, the more intense the air heat exchange between the material in the pipe and the surface of the pipe, and the greater the temperature difference. The greater the length and width of the crack, the more likely the water damage will occur in the future, and the leakage will also be reflected by the severity index. Therefore, the more severe the crack, the greater the temperature difference between the surface of the pipe and the crack, and we can use the thermal imager to detect the temperature difference and then detect the severity of the leak.

Through the research, it is found that the illumination will affect the temperature of the pipe surface and the crack temperature at the same time, hence has little effect on their temperature difference. The illumination only has a great impact on the temperature between the pipe surface and ambient environment, as shown in FIG. 3. Under the same conditions, the higher the temperature, the greater the temperature difference between the crack and the pipe surface. However, we need to reflect the severity of the crack through the temperature difference. Therefore, it is necessary to calculate the severity index to determine the temperature difference, and to correct the temperature difference between the crack and the pipe surface under different temperature conditions.

The severity of leakage can be measured in a variety of ways. The present invention is described in terms of length, width, and area, respectively, and defines G as the leakage severity index.

$$G_1 = \left[\frac{l \times r_1}{D} \times 100\% \times 10\right] \qquad (1)$$

where $G_1$ is the severity index in the length dimension of the crack; l means the length of the crack, the unit is the number of pixels; D indicates the outer diameter of the pipe, the unit is mm; $r_1$ is the resolution of the length of each pixel of the camera, in mm/pixel point.

$$G_2 = \left[\frac{\frac{S}{l} \times r_2}{0.2} \times 100\% \times 10\right] \qquad (2)$$

where $G_2$ is the severity index in the crack width dimension; S is the area of the crack, and the unit is the number of pixels; l is the length of the crack, and the unit is the number of pixels; $r_2$ is the resolution of the width of each pixel of the camera, in mm/pixel point.

$$G_3 = \left[\frac{S \times r_1 \times r_2}{\frac{S}{l} \times \frac{\pi D}{2}} \times 100\% \times 10\right] \qquad (3)$$

where $G_3$ is the severity index in the dimension of the crack area; D is outer diameter of the pipe, in mm.

$$G = \frac{G_1 + G_2 + G_3}{3} \qquad (4)$$

G is the severity index of the crack, and the result keeps 1 decimal place.

At the release level, the severity index of pipeline leakage is divided into three levels: light, medium and heavy:

Light: G=[0-2.9];
Medium: G=[3-6.9];
Heavy: G=[7-9.9].

The conventional severity index is between [0-9.9], but it is not excluded that a particularly severe crack causes the index to reach 10 or more, in which case G=9.9. The relationship between environmental temperature increasing and temperature difference is shown in FIG. 4.

The severity of the leakage is mainly measured by the damage that has caused to the pipeline, that is, the potential damage in the near future. The severity of the leak is not only related to the width, length, and area of the crack, but also to the depth of the crack. The greater the damage caused to the pipeline, the greater the possibility of further water damage. At the same time, the corrosion of the material around the crack is also one of the factors affecting the severity of the crack. Therefore, the severity of the leak needs to be considered comprehensively. In the prior art, image analysis can detect the length, width, and area of the crack. The depth of the crack can be detected by laser radar. The naked eye can estimate the corrosion of the material around the crack, but how to accurately and simply reflect the development degree of the crack is an urgent problem to be solved in the project.

Image Acquisition

Obtaining a stable, sufficient quality infrared image is the basis for subsequent processing.

The uncooled focal plane infrared detector uses an infrared detector and an optical imaging objective lens to receive the infrared radiation energy distribution pattern of the measured object and reflect it on the photosensitive element of the infrared detector, thereby obtaining an infrared thermal image. The image corresponds to the heat distribution field on the surface of the object. In general, an infrared camera converts invisible infrared energy emitted by an object into a visible thermal image. The different colors above the thermal image represent the different temperatures of the object being measured. The present invention now uses a mainstream infrared imaging device-uncooled focal plane infrared detector.

When using the infrared camera to collect the fracture zone, the height of the equipment from the surface of the pipe is 0.5-1 m, and the specific height can be 0.5 m, 0.6 m, 0.7 m, 0.8 m, 0.9 m, 1.0 m. Image processing is required for crack recognition. The resolution of the image taken with the thermal imager is at least 384×288, at 30° C., the thermal sensitivity is at least 0.06° C.; the shooting frame rate is at least 50 Hz, which is used to collect the infrared image of the water pipe under experimental temperature. The main imaging parameters of the DM60-S online thermal imaging camera can be used as a reference for obtaining infrared image equipment.

Similarly, the ordinary image acquisition device and the infrared camera constitute a binocular camera, and the angle of the view of the two pictures is required to be consistent. The ordinary image and the infrared image collected at the same time have the highest repeatability, and the data acquisition end is designed to cover a full area.

The infrared camera can be shot with a fixed location. Since the detection equipment is fixed, the data is irreversible, continuous and trending due to the characteristics of leakage.

The irreversible pointer refers to the picture data of the suspicious leakage point collected by the infrared camera. If there is a leakage crack at the previous moment, the next moment should also exist.

The continuity refers to the fact that the leakage velocity of the leakage crack is relatively slow, usually 1 hour is the detection interval, and the parameters of the leakage crack at the latter moment should only be slightly changed based on the parameters of the leakage crack at the previous moment. On the infrared image, the color of the infrared image and the dimensional parameter curve of the possible leakage crack should be smooth and the change is minimal.

Among them, the trend indicates that since the leakage crack is irreversible, the crack at the latter moment must be greater than or equal to the crack from the previous moment. In the infrared image, the color of the infrared image will not change or deepen, and the size parameter of the leaking crack may change or become larger.

Temperature measuring fiber sensor is disposed in the pipeline corridor, and the detection result is transmitted to the distributed fiber temperature sensing host through the temperature measuring fiber sensor, and the sensing host analyzes and processes the collected signal in real time to realize the monitoring work of the heating pipe. At the same time, the distributed or robotic inspection type infrared temperature sensing system monitors the temperature field in the pipeline corridor environment in real time, and assists the sensing devices such as cameras and sensors configured in various areas of the pipeline corridor through the transmission link. The information is processed by the sub-control center and collected in the monitoring center. Among them, the temperature abnormality detection data of the optical fiber sensor is used as a control for the detection of the infrared temperature sensing system, and the trade-offs and corrections of the results are as follows (second correction of measured temperature difference data):

(1) When the results of the two are the same, the test is considered correct;

(2) When the results of the two are different, if the result of the fiber optic sensor indicates that leakage has occurred, and the infrared temperature sensing system shows that no leakage has occurred, it is considered that leakage has occurred; if not, it is considered that no leakage has occurred;

(3) When one instrument does not have feedback data, the result of another data is taken;

(4) When there is no feedback data, the system is considered to be faulty and needs to be timely repaired.

Among them, the infrared thermal imaging image acquisition system is composed of DM60-S model infrared thermal imager and JVS-C300Q model data acquisition card. The infrared thermal imager is used to capture the infrared image of the monitoring area, and the acquisition card assists in collecting thermal imaging image storage. It is easy to call and process at any time on the computer hard disk. At the same time, inspection robot is used for assisting, and 360 camera equipment is installed. The machine is equipped with WIFI device to realize real-time transmission of data information, and it can realize fast and accurate leak inspection at any time.

The infrared camera can also be placed on the mobile inspection equipment for regular inspection. The mobile inspection technology currently exists for three generations.

The first generation of mobile patrol technology based on SMS has many serious flaws. The most serious problem is that the real-time performance is poor, and the query request will not be answered immediately. In addition, due to the limitation of the length of the SMS message, some queries cannot get a complete answer.

The second-generation mobile patrol system adopts the WAP technology-based approach. The mobile phone mainly accesses the WAP webpage through the browser to realize the information query, and partially solves the problem of the first-generation mobile access technology. The shortcomings of the second generation of mobile access technology mainly show that the interactive ability of WAP web access is poor, thus greatly limiting the flexibility and convenience of the mobile inspection system. In addition, because the secure channel established by the WTLS protocol used by the cryptographic authentication of the WAP must be terminated on the WAP gateway, a security risk is formed, so the security problem of the WAP webpage access makes the second-generation technology difficult to meet the requirements of the user.

The new generation of mobile patrol system, the third-generation mobile patrol system, combines the latest mobile communication, information processing and computer networks such as 3G mobile technology, smart mobile terminals, VPN, database synchronization, identity authentication, and Web service. Frontier technology, relying on private network and wireless communication technology, has greatly improved the security and interaction capabilities of the system, providing a safe and fast modern mobile law enforcement mechanism for patrol personnel.

The mobile inspection system can realize the on-site inspection record of lines, pipelines, equipment, etc., the photographing function, the positioning function, the patrol track playback function, the task tracking function, the position of the equipment and the display function distributed on the map.

Based on the Matlab program, a frame image is extracted from the video collected by the mobile inspection device. The specific implementation is to use the program to read a frame, save a frame, then empty and recycle.

Image Processing

In practical applications, various environmental disturbances will seriously affect image quality of the cracks, which makes it difficult to detect cracks in the later stage. Therefore, image preprocessing is very necessary. Preprocessing can remove some redundant information in the image and highlight the target we are interested in, so as to reduce the amount of image information and improve the image quality. To this end, it is necessary to preprocess the captured image, which mainly includes several steps of image graying, noise reduction, edge detection or threshold segmentation, opening and closing operations, region segmentation, and crack geometric information recognition.

The acquired infrared image of the leaking crack is a color image containing brightness and color information, etc. It is necessary to grayscale the crack image, that is, to convert the originally collected color image into a grayscale image, and remove the color information in the image. The color of each pixel in the color image is determined by three components: R, G, and B. One pixel can have a variation range of more than 16 million (255*255*255) colors. The grayscale image is a special color image with the same R, G, and B components, with the range of one pixel varying from 255. Therefore, in digital image processing, images of various formats are generally converted into gray images to reduce the amount of subsequent image calculations. The description of the grayscale image, like the color image, still reflects the distribution and characteristics of the overall and local chromaticity and brightness levels of the entire image. Grayscale processing of images can be achieved in two ways.

The first method is to find the average of the three components of R, G, and B for each pixel, and then assign this average to the three components of the pixel.

The second method is based on color space of YUV. The physical meaning of the component of Y is the brightness of the point, and the brightness level is reflected by the value. The brightness Y and R, G, B can be established according to the change relationship of the color space of RGB and YUV. The correspondence of the color components: Y=0.3R+0.59G+0.11B, and the gray value of the image is expressed by this brightness value.

The brightness of the leaky crack image collected by the traditional image-based method is not uniform, and the gray value of the crack part and the background part of the image has a large difference. This large difference will bring certain difficulties to the subsequent processing, such as the selection of thresholds in image segmentation. However, the present invention introduces an infrared image by using an ordinary image for crack recognition, and the image thereof is only caused by the difference in temperature. In the experimental environment described above, the image is collected without substantially having a temperature difference. Therefore, the present invention does not need to consider the impact of gray unevenness.

Image denoising is suitable for ordinary images and infrared images. In reality, digital images are often affected by imaging equipment and external environmental noise during digitization and transmission, and are called noisy images. The process of reducing noise in digital images is called image denoising. Noise is an important cause of image interference. An image may have a variety of noises in practical applications, which may be generated in transmission or may be generated in processing such as quantization. According to the relationship between noise and signal, it can be divided into three forms: f(x,y) represents a given original image, g(x, y) represents an image signal, and n (x, y) represents noise.

(1) Additive noise, which is independent of the input image signal. The noisy image can be expressed as f(x, y)=g(x,y)+n(x,y), channel noise and light guide tube noise generated when the camera scans the image are such noise;

(2) Multiplicative noise, which is related to the image signal. The noisy image can be expressed as f(x, y)=g(x,y)+n(x,y)g(x,y), flying point noise when the scanner scans the image, the coherent noise in the TV image, and the particle noise in the film are such noise.

(3) Quantization noise, which is independent of the input image signal, is the quantization error in the quantization process, and is reflected in the receiving end.

Noise can generally be defined as unpredictable in theory, and random errors can only be recognized by probabilistic methods. Therefore, it is more appropriate to regard the noise in the image as a multi-dimensional random process. The random process can be used to describe the noise, that is, the probability distribution function and the probability density distribution function are used to represent, and there are several mature noise reduction algorithms can be used. The methods of image noise reduction mainly include the following types:

(1) Mean Filter

The mean filter using the neighborhood averaging method is very suitable for removing particle noise in an image obtained by scanning. The field averaging method strongly suppresses the noise, and at the same time causes the ambiguity due to the averaging, and the degree of ambiguity is proportional to the radius of the neighborhood. The smoothness achieved by the geometric mean filter can be compared to an arithmetic mean filter, but less image detail is lost during the filtering process. Harmonic averaging filters work better for "salt" noise, but not for "pepper" noise. It is good at dealing with other noises like Gaussian noise. The inverse harmonic mean filter is more suitable for processing impulse noise, but it has the disadvantage that it must be known whether the noise is dark noise or bright noise, in order to select the appropriate filter order symbol. If the symbol of the order is wrong, catastrophic consequences may be caused.

(2) Adaptive Wiener Filter

It can adjust the output of the filter according to the local variance of the image. The larger the local variance, the stronger the smoothing effect of the filter. Its ultimate goal is to minimize the mean square error $e2=E[(f(x,y)-f\hat{}(x,y)2)]$ of the restored image $f\hat{}(x,y)$ and the original image $f(x,y)$. The filtering effect of this method is better than that of the Mean filter, and it is useful for retaining the edges and other high-frequency parts of the image, but the calculation amount is large. The Wiener filter has the best filtering effect on the image with white noise.

(3) Median Filter

It is a commonly used nonlinear smoothing filter. Its basic principle is to replace the value of a point in a digital image or a digital sequence with the median value of each point value in a field of the point. Its main function is to make the surrounding pixels gray. A pixel with a large difference in degree value is changed to a value close to the surrounding pixel value, so that an isolated noise point can be eliminated, so the median filtering is very effective for filtering the "salt" and "pepper" noise of the image. The median filter can remove both noise and edges of the image to obtain a satisfactory restoration effect. Moreover, the statistical characteristics of the image are not required in the actual operation, which brings a lot of convenience. However, Median filter should not be used on images with more details, especially those with more points, lines and apex details.

(4) Morphological Noise Filter

Combining the opening and closing can be used to filter out the noise. First, the noisy image is turned on. The structural element matrix can be selected to be larger than the noise, so the result of the turning on is to remove the noise on the background. Finally, the image obtained in the previous step is closed to remove the noise on the image. According to the characteristics of this method, the image type to which this method is applicable is that the size of the object in the image is relatively large, and there are no fine details.

(5) Wavelet Denoising

This method preserves most of the wavelet coefficients that contain the signal, so the image detail can be better preserved. There are three main steps in image denoising by wavelet analysis: wavelet decomposition of image signals; threshold quantization of high-frequency coefficients after hierarchical decomposition; reconstruction of image signals by two-dimensional wavelets.

Edge detection is a fundamental problem in image processing and computer vision. The purpose of edge detection is to identify points in the digital image where the brightness changes significantly. Significant changes in image properties often reflect important events and changes in attributes. These include (i) discontinuities in depth, (ii) discontinuities in surface orientation, (iii) changes in material properties, and (iv) changes in scene illumination. Edge detection is a research field in image processing and computer vision, especially feature extraction.

There are many methods for edge detection, which can be broadly divided into two categories: search-based and zero crossing-based. The search-based edge detection method firstly calculates the edge intensity, usually expressed by a first derivative (such as local gradient mode). Then it uses the calculation to estimate the local direction of the edge, usually using the direction of the gradient, and uses this direction to find the maximum value of the local gradient mode. The zero-crossing based method finds the zero-crossing of the second derivative derived from the image to locate the edge. The zero-crossing point of a Laplacian or a nonlinear differential equation is usually used. Filtering is usually necessary as a pre-processing of edge detection, with Gaussian filtering usually used. The published edge detection method applies a measure of the calculated boundary strength, which is fundamentally different from smoothing filtering. They use different kinds of filters to estimate the gradients in the x-direction and the y-direction, as many edge detection methods do, relying on the calculation of image gradients. Commonly used edge detection templates include Laplacian operator, Roberts operator, Sobel operator, log (Laplacian-Gauss) operator, Kirsch operator and Prewitt operator.

Secondly, using infrared thermal images, combined with threshold segmentation to extract temperature difference points. The temperature difference between the leak point and the surrounding area is the difference between the RGB values reflected in the gray scale. Therefore, the temperature difference point can be extracted when the appropriate threshold is set.

Compared with the background, the crack target that needs to be identified in the images has less information. Besides, in the process of image acquisition and transmission, the resolution and contrast of the image are reduced due to interference of many factors. Therefore, after filtering and denoising the image, the graphics are further enhanced, so that the crack target that we are interested in is more prominent, providing a basis for the subsequent segmentation recognition algorithm.

Image threshold segmentation is a widely-used segmentation technique. Based on the difference between the target region and the background in the image, the image is treated as two types of regions (target region and background region) with different gray levels. The combination of a reasonable threshold is selected to determine whether each pixel in the image should belong to the target area or the background area, thereby generating a corresponding binary image. The purpose of this step of the invention is to find the crack area and the non-crack area. The characteristic of the threshold segmentation method is that it is suitable for the case where the target has a strong contrast with the background gray scale. It is important that the gray scale of the background or the object is relatively simple, and the boundary of the closed and connected region can always be obtained. Whether in grayscale images or infrared images, the grayscale or color of cracks and pipes have obvious differences, and it is suitable to use image threshold segmentation algorithm. The advantage of threshold segmentation is that the calculation is simple, the operation efficiency is high, and the speed is fast. Thus, it can be used in applications where operational efficiency is important.

The process of the image threshold segmentation algorithm can be represented by FIG. 5. First, a model is built and the original signal is characterized by the features of the model. In the field of image threshold segmentation, the model can be a one-dimensional histogram or a two-dimensional histogram, etc. Whether the model is reasonable or not is directly related to the results of subsequent processing. The more information is considered, the larger the calculation amount will be. For example, the image segmentation method based on two-dimensional histogram has more calculation amount than the one-dimensional histogram based segmentation. The second step of threshold segmentation is to determine the criterion for obtaining the threshold. In the case of a certain model, the criterion for determining the threshold determines the final segmentation threshold. There are many criteria for obtaining the threshold, such as the maximum entropy method and the maximum inter-class variance. The third step of threshold segmentation is to obtain the segmentation threshold. In the case that the model established in the first step of threshold segmentation is not complicated, the exhaustive method can achieve good results; if the model established in the first step is more complicated, it takes a lot of time to implement the method, which is not conducive to practical application. At this time, using the group intelligence algorithm to obtain the threshold, such as the particle swarm algorithm to find the threshold, is a good choice.

According to the classification of images, the image threshold segmentation method can be divided into single threshold segmentation method and multi-threshold segmentation method. If an image has only target and background, a threshold can separate the target from the background. This method is called the single threshold segmentation, if the image needs to be divided into multiple classes, or there are multiple different regions in the image, multiple thresholds are needed to separate them. This is called multi-threshold segmentation. Let the original image be f(x, y), the result of the segmentation is g(x, y), T is the segmentation threshold obtained, and the single threshold segmentation method can be defined as $$g(x, y) = \begin{cases} 1, & \text{when } f(x, y) > T \\ 0, & \text{when } f(x, y) \leq T \end{cases} \quad (5)$$

In the multi-threshold segmentation method, the original image is set as f (x, y), and the segmented result as g (x,y), $T_0, T_1, \ldots T_k$ is a series of segmentation thresholds, and the multi-threshold method can be defined as $$g(x,y)=k, \text{ when } T_k < f(x,y) \leq T_{k+1}, k=0,1,2n. \quad (6)$$

where k is a label of each different region in the divided image. The accuracy of extracting temperature difference points is shown in Table 1.

TABLE 1

The Accuracy of Image Threshold Segmentation Method to Extract Temperature Difference Points

| Ambient heating (° C.) | Actual area of the fracture zone (pixels) | Area extracted by the segmentation algorithm (pixels) | Accuracy (%) |
|---|---|---|---|
| 0 |  | 335.00 | 90.05 |
| 2 |  | 339.00 | 91.13 |
| 4 |  | 352.00 | 94.62 |
| 6 |  | 356.00 | 95.70 |
| 8 | 372.00 | 347.00 | 93.28 |
| 10 |  | 349.00 | 93.82 |
| 12 |  | 351.00 | 94.35 |
| 14 |  | 352.00 | 94.62 |
| 16 |  | 364.00 | 97.85 |

Edge Extraction and Image Segmentation

The edge extraction method is then used to accurately extract, classify and locate the cracks.

The traditional crack analysis technology based on image analysis only pays attention to the crack itself. It is necessary to detect the presence or absence of cracks, with location and geometry information, and the transition between the crack and the pipeline is basically not considered. The present invention mainly needs to obtain the temperature difference between the pipeline area and the crack area. It is necessary to pay attention to the two areas of the crack and the pipeline. Therefore, the influence of the transition area can be considered. After the crack and the pipeline area are obtained by image segmentation, the boundary transition between the two regions is required. The area is cut off because the temperature of the pipe to the crack is gradual. The temperature of the transition zone between the crack and the pipe is between the center temperature of the crack and the temperature of the pipe. The transition area is the interference zone when acquiring the pipe temperature, as shown in FIG. 6. The following measures can be taken to eliminate the interference zone.

For the pipeline area, the transition interference zone is small relative to the area of the pipeline area. Therefore, when the exclusion is made, a fixed width can be adopted for the reduction of the pipeline area, where the width can be set to w (0.5 mm<w<2.5 mm). In fact, it is also possible to adopt a method based on the maximum width ratio of the crack region. Because after detecting the crack region, the crack region is increased by one time up and down, and the remaining region is defined as a pipeline region without interference zone, assuming the width of the segmented road surface is $D_0$, and the final width is determined by the following formula (7). This method can better eliminate the influence of the transition interference zone.

$$D=D_0-2d_0 \quad (7)$$

For the crack area, due to the width is small, the exclusion of the transition interference area needs to be more detailed. It can be excluded by the method based on the width ratio of the crack area. The crack area of the image segmentation needs to be slimmed down, assuming the width of the crack is d, the width of the segmented crack region is $d_0$, they meet the following equation (8):

$$d_1=d_0-2\alpha d_0 \quad (8)$$

where $\alpha$ is the ratio of the upper and lower parts of the crack width to eliminate the transition interference zone, $0.1 \leq \alpha \leq 0.2$.

After the range of the transition interference zone is determined, how to delete it specifically can refer to the following: 1) For the pipeline area, it is equivalent to moving the image segmentation boundary $d_0$ along the segmentation boundary radially toward the pipe zone to obtain a new pipe zone boundary. 2) For the crack zone, the image segmentation boundary is moved $d_0$ along the segmentation boundary radially toward the crack region to obtain a new crack region boundary.

In digital images, the edge is the main part of the local intensity change of the image, mainly between the target and the background. By detecting the edges, the image information to be processed is greatly reduced, and the shape information of the objects in the image is retained. Edge detection is a matrix convolution operation on an image using a template. The convolution operation is to multiply each pixel in the image region used by each element of the template (weight matrix), and the sum of all products is the new central pixel value for that region.

$$R = \begin{bmatrix} R_1 & R_2 & R_3 \\ R_4 & R_5 & R_6 \\ R_7 & R_8 & R_9 \end{bmatrix},$$

Convolution matrix $$G = \begin{bmatrix} G_1 & G_2 & G_3 \\ G_4 & G_5 & G_6 \\ G_7 & G_8 & G_9 \end{bmatrix},$$

The new center pixel value can be expressed as $R_5(\text{centerpixel}) = R_1G_1 + R_2G_2 + R_3G_3 + R_4G_4 + R_5G_5 + R_6G_6 + R_7G_7 + R_8G_8 + R_9G_9$, Thereafter, a sobel operator consisting of a gradient and a difference principle is used in the digital image detection method. It is a weighted average operator that highlights the edges by weighting them to the center point. At the same time, the image segmentation algorithm with adjustable threshold is used to distinguish the crack from the background, and the crack region and impurity with lower gray value are converted into black, and the background with higher gray value is converted to white. In addition, the introduction of the area threshold and the area-circumference fractal law remove non-cracked areas such as impurities, and only maximize the crack area.

To use open and close operations, firstly we need to understand corrosion and expansion. Corrosion is a process to eliminate the boundary point and make the boundary shrink to the inside, which can be used to eliminate small and meaningless objects; Expansion is the process of merging all background points in contact with an object into the object, expanding the boundary to the outside, which can be used to fill holes in objects. Open operation: the process of firstly eroding and then expanding. It is used to eliminate small objects, separate objects at slender points, and smooth the boundaries of larger objects without significantly changing their area. The open operation is usually used when it is necessary to remove small particle noise and to break the adhesion between the targets. Its main function is similar to corrosion, and it has the advantage of keeping the original size of the target unchanged compared with the corrosion operation. Closed operation: The process of firstly expanding and then eroding. It is used to fill small voids in objects, connect adjacent objects, and smooth their boundaries without significantly changing their area.

Although the corrosion treatment can separate the target of adhesion, the expansion treatment can connect the broken target, at the same time, there is a problem that after the corrosion treatment, the area of the target is smaller than the original area, and after the expansion treatment, larger. Open and closed operations were proposed to solve this problem.

The morphological transformation of binary images in mathematical morphology is a process of processing against sets. The essence of the morphological operator is to express the interaction between the set of objects or shapes and the structural elements. The shape of the structural elements determines the shape information of the signals extracted by this operation. Morphological image processing is to move a structural element in the image, then intersect or merge the structural element with the following binary image.

For the accurate extraction and processing of crack morphology, the calculation method of fractal dimension is adopted. Not all irregular graphics have fractal features, and only graphics that satisfy self-similarity within a certain scale range satisfy the fractal feature. To study the fractal characteristics of pipeline cracks, the key is to calculate whether the fractal dimension values corresponding to the surface cracks of the structure meet the requirements of non-European space. The fractal dimension can quantitatively and qualitatively reflect the degree of damage on the surface of the pipeline. There are many methods for solving fractal dimensions: 1) differential box-counting method; 2) area-circumference method; 3) blanket cover method; 4) fractal Brownian motion self-similar model method; 5) multi-scale fractal method. Here the area-circumference method is used to calculate the fractal dimension and study the fractal law of pipe cracks.

According to the fractal geometry theory, the irregular pattern satisfies the relationship between the circumference and the area: $P^{1/D} \propto A^{1/2}$. P represents the circumference, A represents the area, D represents the fractal dimension, and logarithmically obtained on both sides of the formula:

$$\log P = 0.5D \log A + C \tag{9};$$

where C is a constant. In order to measure the fitting accuracy of the above formula, the linear fitting accuracy is calculated by the following formula. When the $R^2$ value is close to 0, it means that the fitting accuracy is very poor; when the value is close to 1, it means that the fitting accuracy is very high.

$$R^2 = \frac{(n\sum x_i y_i - \sum x_i \sum y_i)^2}{(n\sum x_i^2 - (\sum x_i)^2)(n\sum y_i^2 - (\sum y_i)^2)} \tag{10}$$

Firstly, the clear, complete and undisturbed pipe crack image is converted into a binary image by adaptive threshold segmentation, and the crack is extracted as a black region. Then the boundary tracking method is used to calculate the crack area and perimeter in the formula. The number of pixels in the unicom area is the area of the crack. The number of pixels on the statistical boundary is the perimeter of the crack. Finally, the area and perimeter values are substituted into the former formula, and the least squares method is used. Linear equation of area-circumference relationship in double logarithmic coordinates is obtained to find the fractal dimension of the crack D. Calculation is completed by selecting 10 clear, complete cracks.

By analyzing the data, the area-circumference relationship of the crack can be obtained as:

$$\log P = 1.0289 \cdot \log A - 0.4211 \tag{11}$$

The fitting degree is: $R^2 = 0.9957$. It indicates that the straight line of the crack on the pipe surface conforms to the fractal law and has a high fitting precision. For comparison, 10 impurities of different sizes and shapes were selected in the image, and the same fitting calculation was performed to obtain the relationship between the area and the circumference:

$$\log P = 1.024 \cdot \log A - 0.27 \quad (12)$$

The fitting degree here is: $R^2 = 0.9165$.

Define the function below: $F(P, A) = \log P - 1.0289 \cdot \log A + 0.4211$

For pipe cracks, the following formula should be satisfied within a certain margin of error: $F(P, A) \approx 0$.

In the actual pipeline surface image, due to the existence of various interferences and pollution, the above formula is generally not automatically satisfied. To this end, a crack detection method combining skeleton extraction and fractal features is proposed, which is to optimize the position of the crack edge obtained after image segmentation to meet the requirements of the formula. The flow of the crack extraction algorithm combined with the skeleton and fractal features proposed in this invention is shown in FIG. 7. The fractal dimension of the crack and impurity regions is as shown in FIG. 8.

After obtaining the infrared image, the image needs to be processed to obtain the temperature data of the pipe crack and the pipe, and then for further analysis.

From the gray-scale information of the infrared thermal image, the crack region and the pipeline surface region can be obtained by using the existing mature algorithm. And then the RGB average value of the image in each region is obtained, and finally the average RGB value is matched with the colorbar, from left to right by two-pixel width to ensure the accuracy of the temperature value. Then, it calculates the temperature value according to the matched position and color range.

Image area feature analysis is the ability of a computer to recognize an image, that is, image recognition. Feature selection is a key issue in image recognition. The basic task of feature selection and extraction is how to find the most effective features from a multitude of features.

According to the image to be identified, a set of original features is generated by calculation, which is called feature formation. The number of original features is large, or the original sample is in a high-dimensional space. The feature description in high-dimensional space can be described by the feature of low-dimensional space through mapping or transformation. This process is called feature extraction. Some of the most effective features are selected from a set of features to achieve the goal of reducing the dimension of the feature space. This process is called feature selection.

In addition to color features, shape features are an important aspect for distinguishing image features. Concavity and convexity is one of the basic features of a region. The concavity and convexity of a region can be determined by a method: If a line connecting any two pixels in a region passes through a pixel outside the region, this region is concave; Conversely, if a line connecting any two pixels does not pass through pixels other than this figure, this region is convex. The smallest convex area containing any graphic is called the convex closure of this graphic. After removing the portion of the original graphic from the convex closure, the position and shape of the resulting graphic will be an important clue for shape feature analysis.

Based on the regional characteristics of the leak point, such as roundness, density, and other parameters, we determine the type of leakage of a known leak point. When a certain characteristic of the leakage area satisfies the following conditions, it can be considered that the leakage area at this point is such type of leakage. This section mainly considers the perimeter/area of a leaking area and the area of the circumscribed rectangle of the leaking area $S_1$/the area of the area $S_2$.

If the perimeter/area of a leaking area is >0.5, the leak is considered to be a crack;

As shown in FIG. 9(a), it is assumed that when a leaking region is a perfect circle, and a circular radius is set as r, and the crack width is r/5, the area of the circumscribed rectangle of the leaking region $S_1$/the area of the region $S_2$ can be expressed as follows:

$$S_1/S_2 = 2r \cdot r / \pi r \cdot \frac{r}{5} = 3.18 \quad (13)$$

As shown in FIG. 9(b), for the extreme assumption that a leaky region is an absolute crack, the crack width is r/5, and the length is πr, the area of the circumscribed rectangle of the leaking region $S_1$/the area of the region $S_2$ can be expressed as follows:

$$S_1/S_2 = \pi r / \pi r = 1 \quad (14)$$

Therefore, if the area of the circumscribed rectangle of the leaking region $S_1$/the area of the region $S_2 > 3.18$, the leak is considered to be loose-like leakage of the interface; if $1 < S_1/S_2 < 3.18$, more detailed is needed to judge.

Using edge extraction and contour tracking technology, in the infrared image, the possible occurrence of leakage in the infrared image can be accurately extracted. And the error caused by factors such as large-area impurities or skin peeling can be avoided according to the method of edge fractal optimization.

Model Establishing

Firstly, we study the relationship between the leakage crack and the temperature difference between the ambient and the leakage.

When using the infrared thermal imager to detect the leakage cracks in the pipeline, after extracting the temperature difference, it determines the relationship model between the leakage crack and the temperature difference between the pipeline and the leakage, and then establishes the discriminant model of leakage by combining machine learning technology.

Since the specific heat capacity of the pipe and the volume of water is different, the water temperature and the pipe temperature will be significantly different when the ambient temperature exceeds a given value. Table 2 shows the determined temperatures for leaks and undamaged points at different ambient temperatures.

TABLE 2

| | Group 1 | | Group 2 | | Group 3 | |
|---|---|---|---|---|---|---|
| Ambient heating | Leakage point | Undamaged point | Leakage point | Undamaged point | Leakage point | Undamaged point |
| 0 | 24 | 24 | 24 | 24 | 24 | 24 |
| 2 | 24.4 | 24.6 | 24.2 | 26.4 | 23.8 | 25.6 |
| 4 | 25.2 | 26.2 | 24.4 | 27.9 | 23.4 | 26.2 |
| 6 | 24.3 | 25.5 | 24.4 | 28 | 23.3 | 25.8 |
| 8 | 25.3 | 27.1 | 24.4 | 28.2 | 23.2 | 25.2 |
| 10 | 25.5 | 27.5 | 24.4 | 28 | 23.1 | 26.1 |
| 12 | 26.1 | 27.5 | 24.4 | 27.9 | 23 | 27 |
| 14 | 25.5 | 28.1 | 24.6 | 28.1 | — | — |
| 16 | 27 | 28.6 | 25 | 28.2 | — | — |

According to the temperature change curve of the three leaks, the leakage temperature change values at each temperature are averaged to obtain an average temperature change curve of the leak, which is a non-destructive area. The angle bisector of the two curves is taken as the boundary of the temperature change trend of the leak and the temperature of the undamaged portion, as indicated by the thick black dotted line in FIG. 10.

The data is linearly classified using SVM. The ambient temperature is plotted on the abscissa, and the temperature difference between the crack and the surface of the pipe is plotted on the ordinate. There are three levels of 1, 2, and 3. The greater the number, the more serious the development is. As shown in FIG. 11, the classification function graph can be obtained. The two classification functions as equation (15) (16).

3, 2 Classification Function:

$$\Delta T_{23} = a_{23}T + b_{23} \quad (15)$$

where T (° C.) is the ambient temperature, $\Delta T$ (° C.) is the temperature difference between the pipeline and the crack; $a_{23}$ is the linear classification function coefficient, the value range is 0.02-0.03, $b_{23}$ is the linear classification function constant term, with the value range 1.80-2.55.

2, 1 Classification Function:

$$\Delta T_{12} = a_{12}T + b_{12} \quad (16)$$

where $a_{12}$ is the linear classification function coefficient, the value range is 0.0075-0.0100, and $b_{12}$ is the linear classification function constant term, with the value range 1.2-1.95.

The test results are based on the following judgments:

Firstly, calculate $\Delta T_{12}$ and $\Delta T_{23}$ according to the environmental thermometer, and then compare the measured $\Delta T$ with $\Delta T_{12}$ and $\Delta T_{23}$; If $\Delta T \leq \Delta T_{12}$, the degree of development is 1; If $\Delta T_{12} \leq \Delta T \leq \Delta T_{23}$, the degree of development is 2; If $\Delta T \geq \Delta T_{23}$, the degree of development is 3.

Data acquisition is now performed on other pipelines to verify the accuracy of the above described test models. From the above analysis, in general, the temperature difference between the surface of the pipe and the crack is mainly related to the temperature, and the temperature difference between the crack and the surface of the pipe and the degree of development of the crack are related, so the crack and the pipe can be detected by the infrared camera. The temperature difference of the surface, and then use the above classification function $l_1$ and $l_2$ to detect the degree of development.

Firstly, it is determined that the detection environment meets the requirements of the dark and humid underground pipeline corridor space and the environmental temperature in the pipeline corridor space are uniformly increased by 4° C. Then the infrared camera is used to collect data, and the ambient temperature is recorded. After processing, the temperature difference between the crack and the pipe surface is obtained, and the development threshold is calculated according to the temperature.

In the current background that most crack detections only focus on quantity, different weights can be given to cracks of different degree of development according to the results of the test model, which provides a more accurate reference for pipeline maintenance and improves social benefits.

Calculation of Area Temperature

The pipeline structure is a belt structure for transporting liquids. The environmental factors and loads are the main causes of pipeline structure damage. The physical characteristics of the pipeline area are relatively consistent. Therefore, in the infrared image, the temperature values of the pipeline area are basically the same. It is convenient to calculate the RGB average value of the whole region after obtaining the pipeline area in the image segmentation.

However, the crack area is usually a slender shape, such as a two-meter-long crack, which may be only a few millimeters wide. In this case, the severity of the same crack may vary greatly. Therefore, for the fracture zone, it is necessary to calculate the RGB value in the sub-region and a higher weight should be given to the area with more serious development. The temperature difference between a crack area and the pipe will be an array, as shown in FIG. 12, different section cracks can get different temperature differences.

For the transverse crack, the effective crack region is divided into the p segments by the straight line along the y-axis direction, and each segment length is arbitrary; for the longitudinal crack, the effective crack region is divided into the p segments by the image along the x-axis straight line, and each segment length arbitrarily; for other types of cracks, no segmentation or angular divided into p segments according to the geometric center of the crack, the center angle corresponding to each segment is arbitrary.

According to the accuracy requirement, the crack region divided by the image can be divided into p(p≥2) segments for consideration. Each segment can be processed according to the technical route described above, that is, image graying, noise reduction, and then image enhancement are performed. After image segmentation, the crack region is obtained and then divided into segments for subsequent processing, including calculating the average RGB value for each segment, and then matching the average RGB value with the color value in the legend to determine the temperature value of the segment, and finally obtaining the segment. The length l of the p fracture zones and the temperature difference ΔT between the fracture zone and the pipe are obtained, as shown in equation (17):

$$l=(l_1, l_2 \ldots l_p) \quad (17)$$

where $l_i$ is the length of the i segment after divided into sections, and the temperature difference array is calculated as shown in equation (18).

$$\Delta T = (\Delta T_1, \Delta T_2 \ldots \Delta T_p) \quad (18);$$

where $\Delta T_i$ is the temperature difference between the i section and the pipe after the section of the crack zone is divided.

Then, the weighted average calculation can be performed according to the following formula (19) to obtain the final measured temperature difference ΔT between the effective pipeline region and the effective crack region.

$$\Delta T = \frac{(T_1 l_1 + \ldots + T_p l_p)}{(l_1 + \ldots + l_p)}; \quad (19)$$

Finally, ΔT is compared with the reference temperature difference data to obtain the parameters related to the degree of development.

Or the developmental index of each segment of the fracture region obtained by the array ΔT is as follows (20):

$$m = (m_1, m_2 \ldots m_p) \quad (20);$$

where $m_i$ is the fracture developmental index of the i section after the fracture zone is divided into sections.

According to the degree of development of the crack, the crack weights of different sections are given, so the final developmental index of the crack can be obtained as follows (21):

$$m' = \frac{(m_1 l_1 + m_2 l_2 + \ldots + m_n l_p)}{(l_1 + \ldots + l_p)}. \quad (21)$$

The calculation results are rounded off to take 1, 2 or 3, which is the three levels of crack development.

In the invention, an average distribution method can be adopted, and then with $l_1 = l_2 = \ldots = l_p$, the formula can be converted into the following form (22):

$$m' = (m_1 + m_2 + \ldots + m_p)/n \quad (22)$$

Data Processing

Infrared image data may have degree of distortion. The determined temperature of the leaked and undamaged points may go beyond the reasonable range. Considering that the leakage has irreversibility, continuity and trend, that is, when there is suspicious leakage crack feedback in the current period, the data of the latter period must also have crack feedback, with the temperature difference between the leak and the non-leakage unchanged or growing. After the edge extraction, it can also be reflected in the leakage crack size parameter unchanged or slowly increasing. So when the data violates the law, it is considered to be distorted. There are two ways to deal with this (first correction of measured temperature difference data):

(1) Discard the distortion data directly and migrate the data of the previous period (the size parameter of the leaking crack) to this period. For example, if there is a temperature difference on the infrared image in the period 1 hour before, the shuffle data is migrated to the distortion data period as it is.

(2) Wait for subsequent data to correct the distortion data period. If a certain data (period B) is distorted compared to the previous period data (period A), it is feasible to wait for data of next period (period C). If the period C data and the period A data are irreversible, continuous, and trending, the period C data is migrated to the period B data. If the time period C data and the time period A data do not meet the above three characteristics, the time period A data is considered to be incorrect and rejected. At this time, the data of the period before the period A is not considered for correction.

In the process of model building, the present invention divides the degree of development into three levels of 1, 2 and 3 by machine learning. SVM, as a classification method, may map the linear inseparable sample in low-dimensional space to a linearly separable sample in a high-dimensional space by kernel function. A linear classifier is calculated by kernel function. There are many commonly used kernel functions, such as linear kernel functions, polynomial kernel functions, radial basis kernel functions, Sigmoid kernel functions, and composite kernel functions.

In the present invention, the linear kernel function is firstly used to classify the 1 and 2 grades to obtain the classification function $l_{12}$, and then classify the 2 and 3 grades according to the data to obtain the classification function $l_{23}$. There is a certain error in the machine learning classification. Some of the cracks that belong to the less developed degree are assigned to the category of more serious development, while the cracks with the heavier development degree are assigned to the lighter. However, there may occur decimal developmental index in the calculation of the average developmental index, causing a certain error in the classification, which can also reflect the relative size. The developmental index of 2.6 is rounded to 3, and 2.4 to 2 in the previous classification method. Yet, the 2.6 developmental index and the 2.4 developmental index calculated by weighting are actually not much different, which has a considerable influence on the decision-making of managers. Therefore, in the calculation of the fracture developmental index, the present invention takes a decimal point to indicate the calculated relative relationship. However, it should be noted that the developmental index of 2.4 is not necessarily more serious than the developmental index of 2.3, because as mentioned above, there is an error in the classification itself, and the integer part of 2 may already be inaccurate. Therefore, in order to avoid such a problem, the present invention determines an error term according to the variance of the weighted average calculation method in the calculation process, that is, the developmental index can take one decimal place and is expressed as m±σ.

The data is linearly classified using a SVM. Taking the ambient temperature as the abscissa, the difference between the crack and the surface of the pipe as the ordinate, the points are drawn. There are three levels of 1, 2, and 3. The larger the number, the more serious the development degree is, and the following two classification functions can be obtained.

3, 2 Classification Function:

$$\Delta T_{23} = a_{23} T + b_{23} \quad (23);$$

where T (° C.) is the ambient temperature, ΔT (° C.) is the temperature difference between the pipeline and the crack; $a_{23}$ is the linear classification function coefficient, the value range is 0.02-0.03, $b_{23}$ is the linear classification function constant term, with the value range 1.80-2.55.

2, 1 Classification Function:

$$\Delta T_{12} = a_{12}T + b_{12} \quad (24);$$

where $a_{12}$ is the linear classification function coefficient, the value range is 0.0075-0.0100, and $b_{12}$ is the linear classification function constant term, with the value range 1.2-1.95.

The test results are based on the following judgments:

Firstly, calculate $\Delta T_{12}$ and $\Delta T_{23}$ according to the environmental thermometer, and then compare the measured $\Delta T$ with $\Delta T_{12}$ and $\Delta T_{23}$; If $\Delta T \leq \Delta T_{12}$, the degree of development is 1; If $\Delta T_{12} \leq \Delta T \leq \Delta T_{23}$, the degree of development is 2; If $\Delta T \geq \Delta T_{23}$, the degree of development is 3.

If the crack area is divided into sections and different weights are given according to the degree of development of the crack, the result calculated by the formula can take one decimal place.

The value of the error term can be obtained by the following formula (25):

$$\sigma = \sqrt{\frac{\sum_{i=1}^{n}(m_i - \overline{m})^2}{n-1}} \quad (25)$$

where $m_i$ is the result after testing multiple times. The standard deviation is obtained from the above formula. According to this, the development index of the crack can be written to one decimal place, and the error is defined by a fixed error term. The error term is obtained experimentally, and the new developmental degree index is written as follows (26):

$$m = m \pm a\sigma \quad (26)$$

where a is the error term coefficient, with the value range is 1-3.

DETAILED DESCRIPTION OF EMBODIMENTS

Definitions

Figure 1:
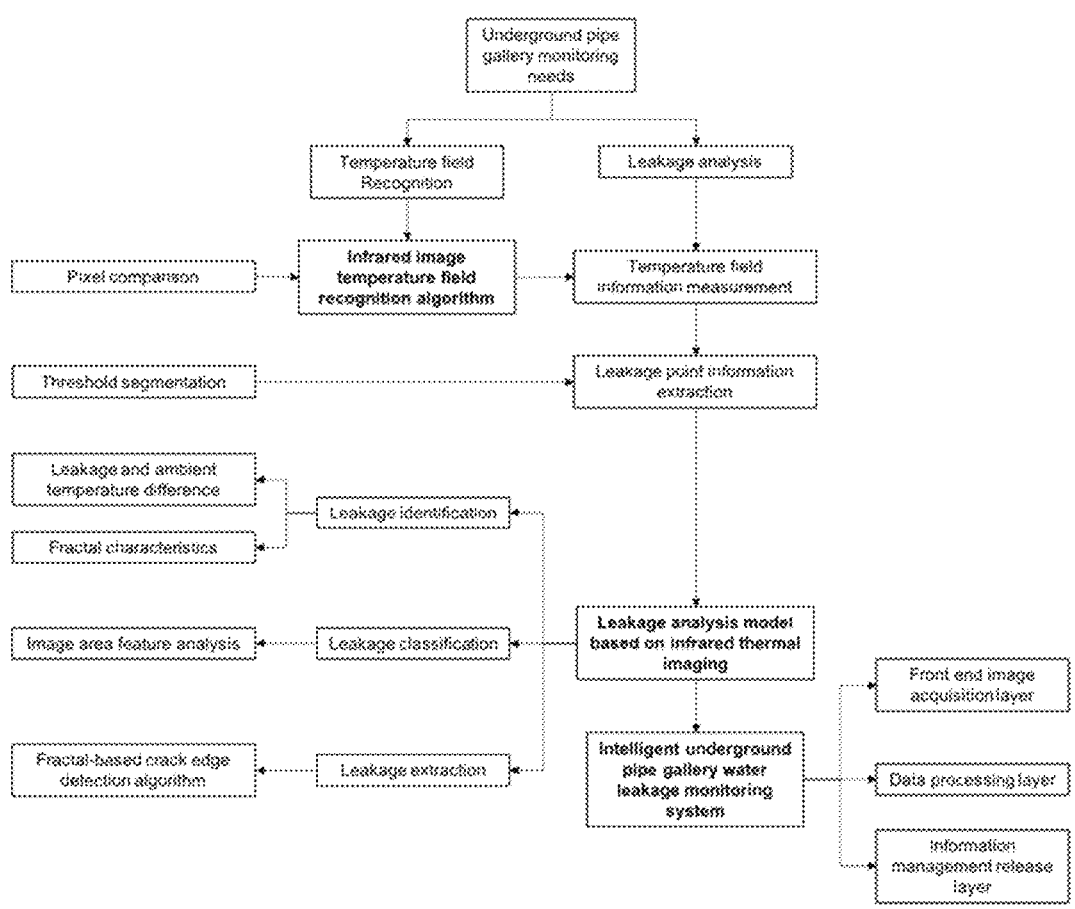
FIG. 1 is a technical diagram for identifying the leakage of the internal space of the pipeline corridor by infrared thermal image.
Figure 2:
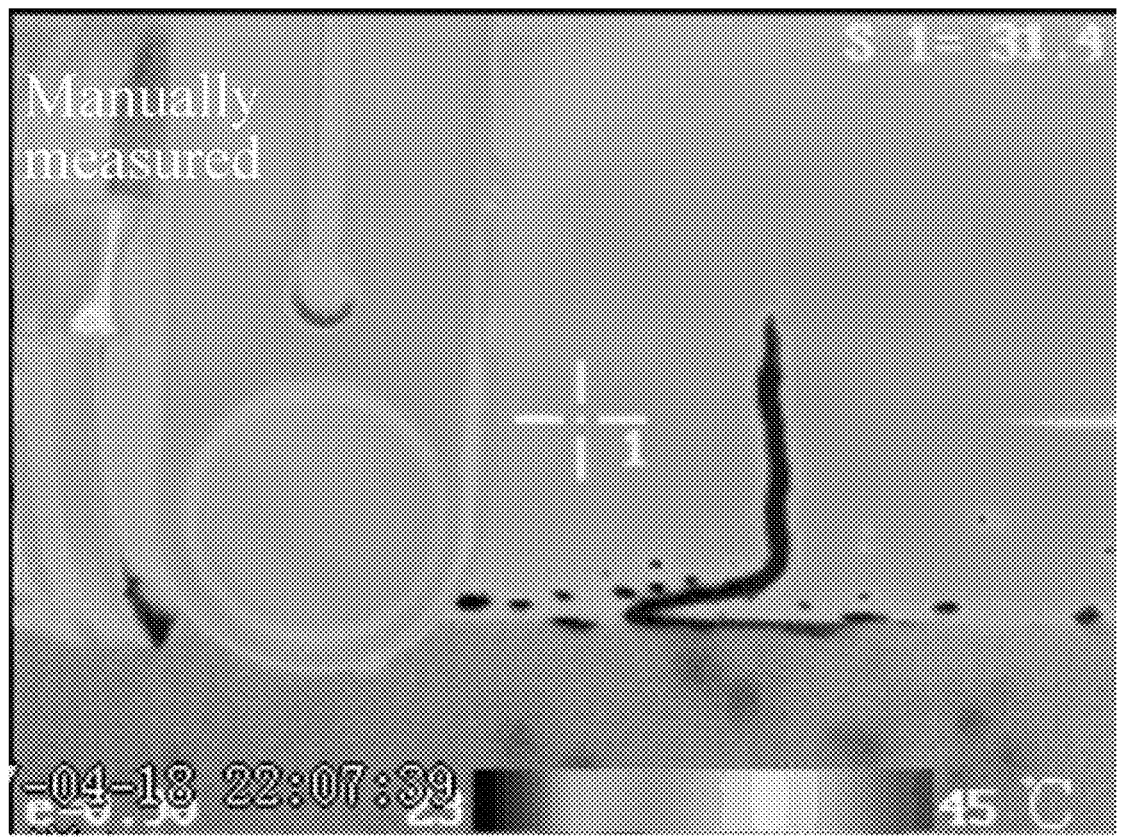
FIG. 2 shows the grayscale information and temperature information of the interior space and cracks of the pipeline corridor.
Figure 3:
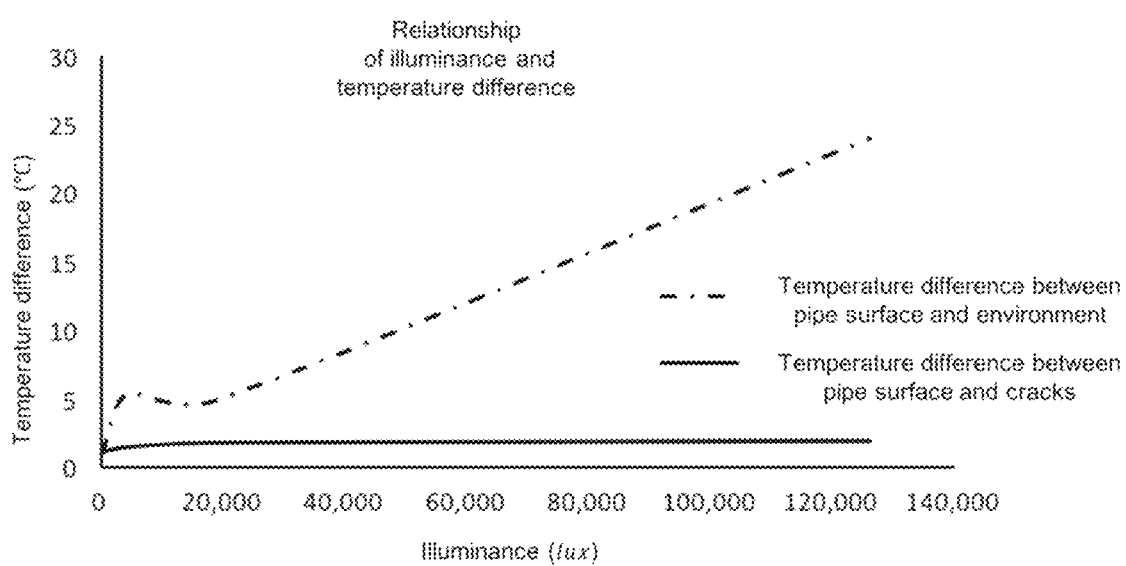
FIG. 3 is a graph of illuminance versus temperature difference.
Figure 4:
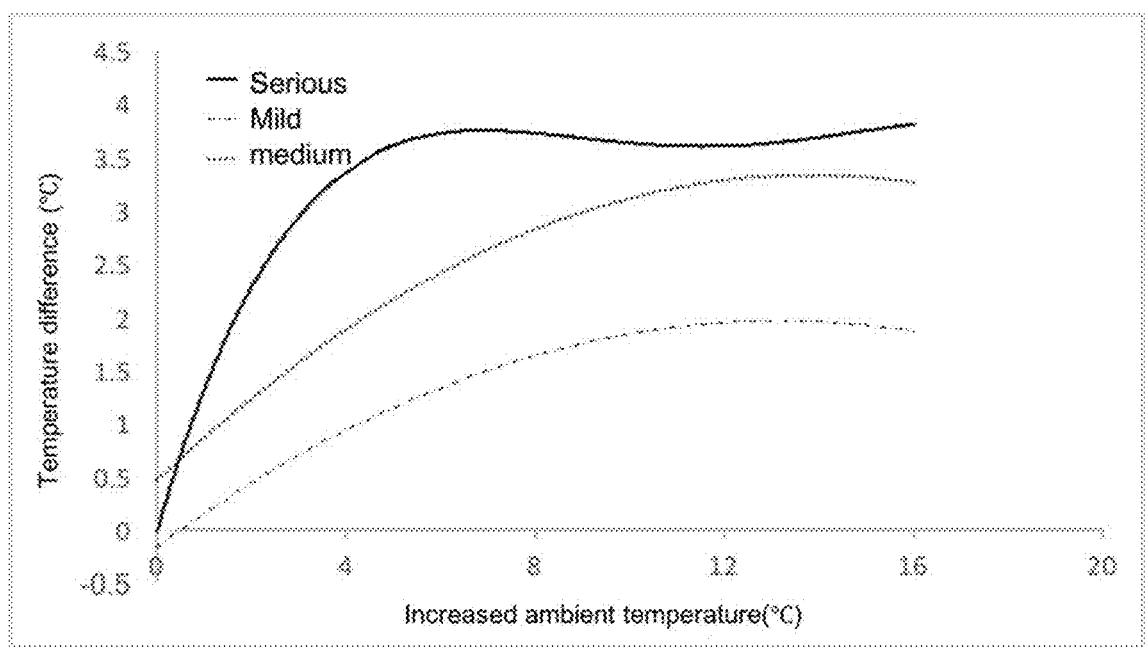
FIG. 4 is a graph showing the relationship between the increase in ambient temperature and the temperature difference.
Figure 5:
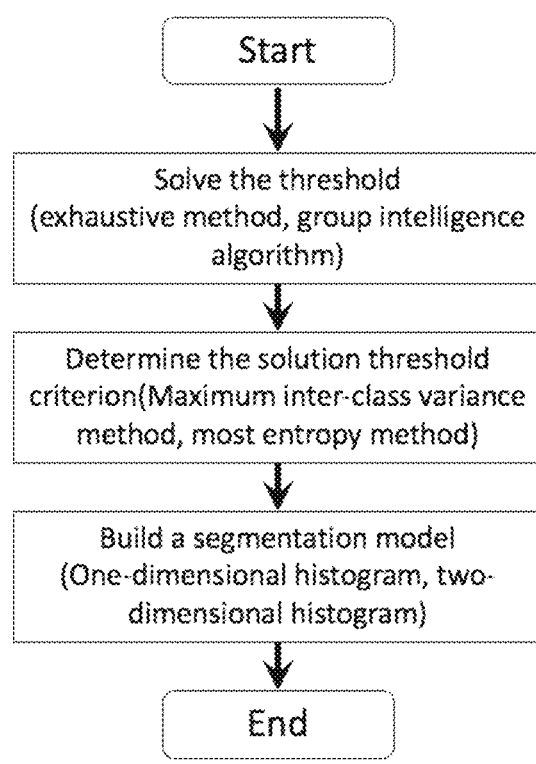
FIG. 5 is an image threshold segmentation model.
Figure 6:
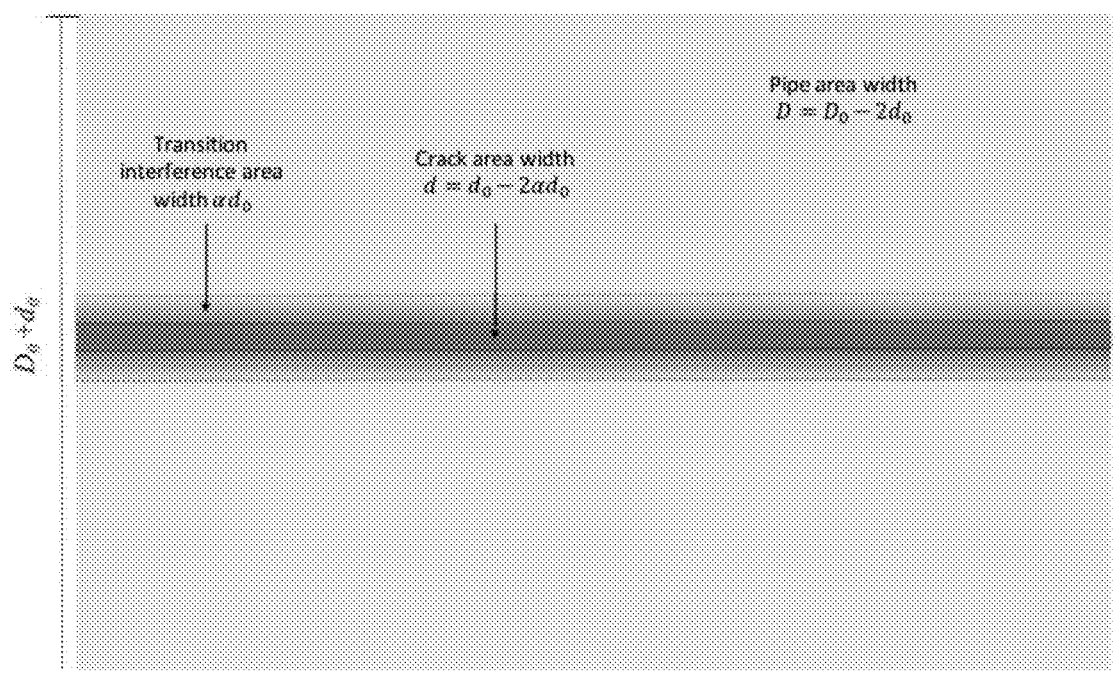
FIG. 6 shows the crack area on the surface of the pipe, the pipe area and the transition interference zone.
Figure 7:
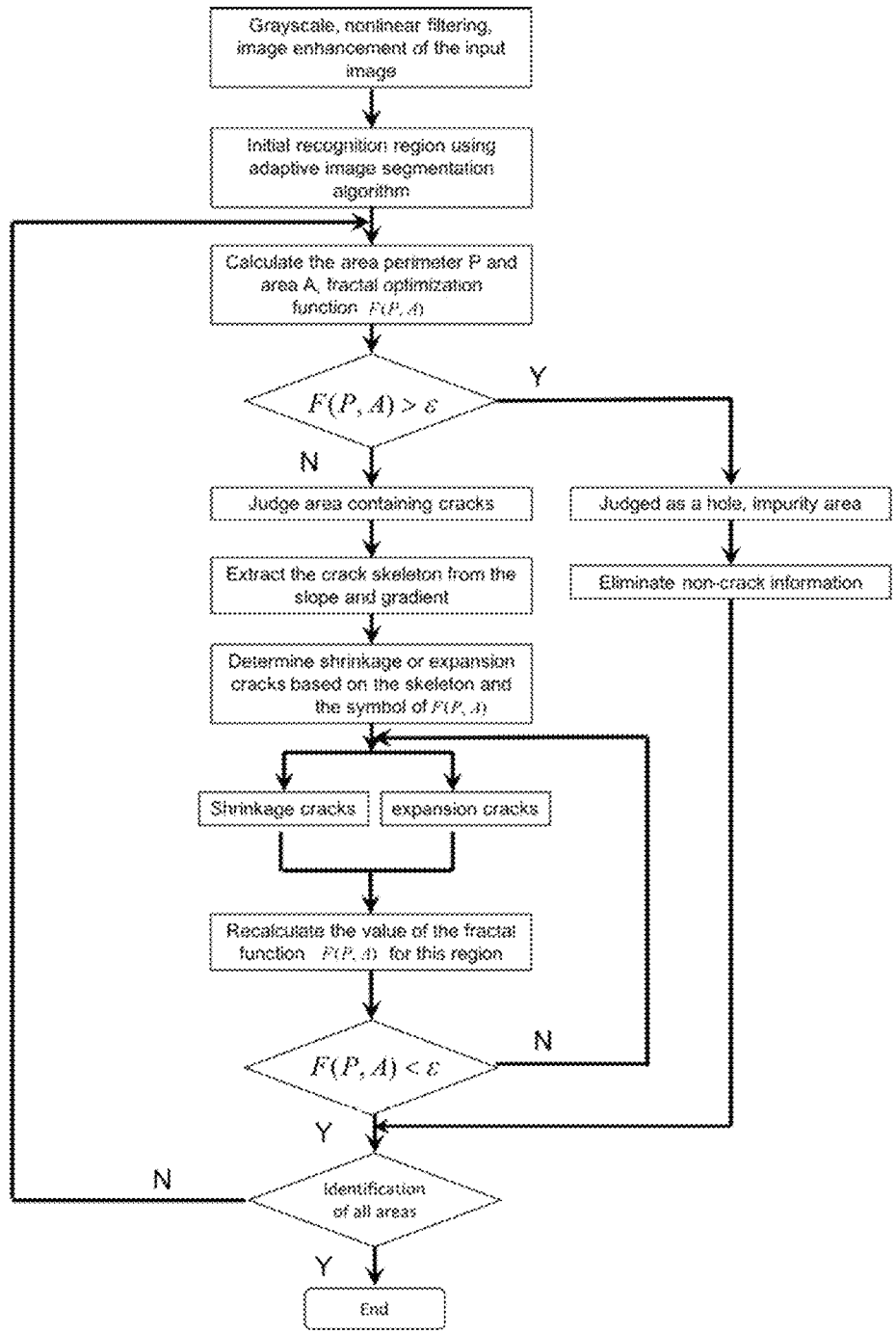
FIG. 7 is a flow chart of a crack extraction algorithm incorporating skeleton and fractal features.
Figure 8:
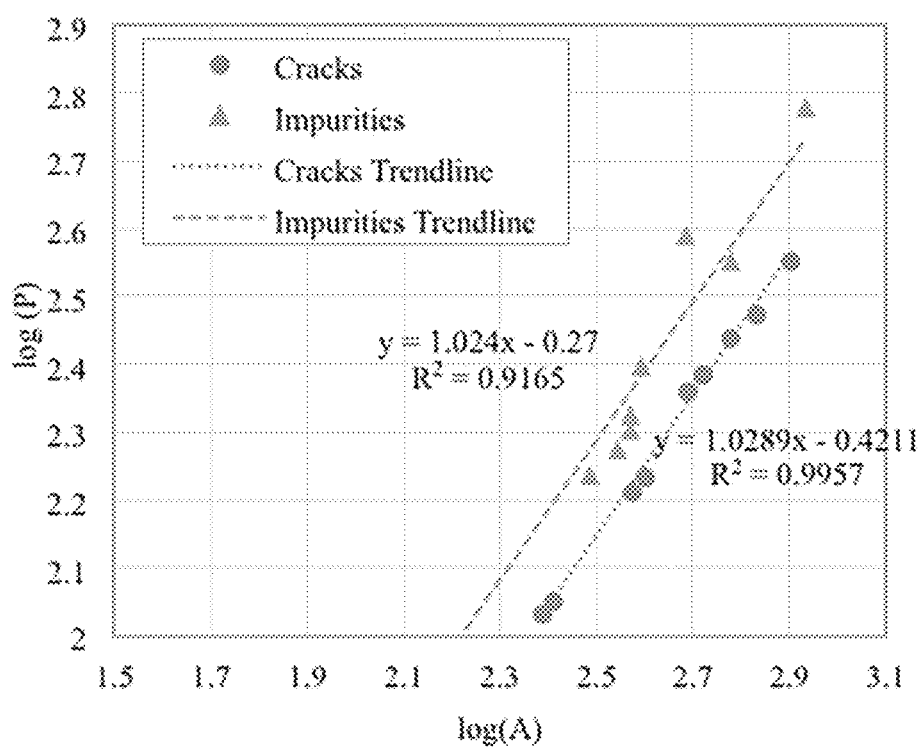
FIG. 8 shows the fractal dimension of the crack and impurity regions.
Figure 9A:
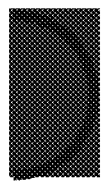
FIG. 9 shows the critical value of looseness leakage at the interface.
Figure 9B:
Figure 10:
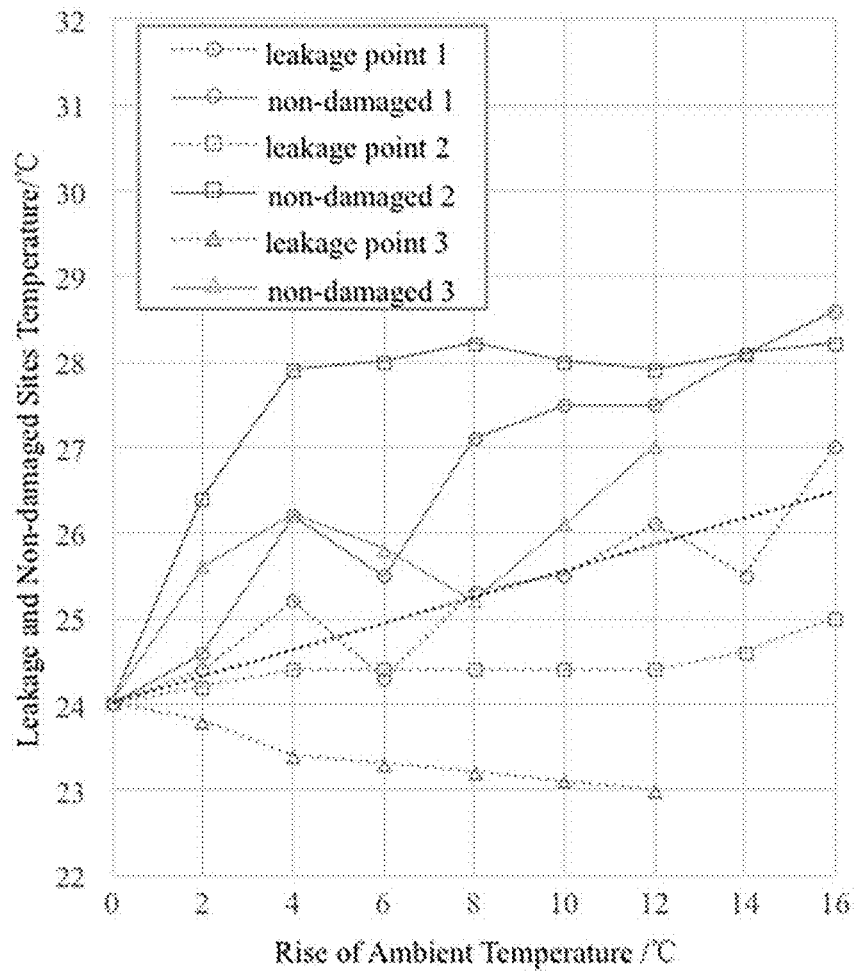
FIG. 10 is a graph showing temperature changes at the leaked and undamaged locations after ambient heating.
Figure 11:
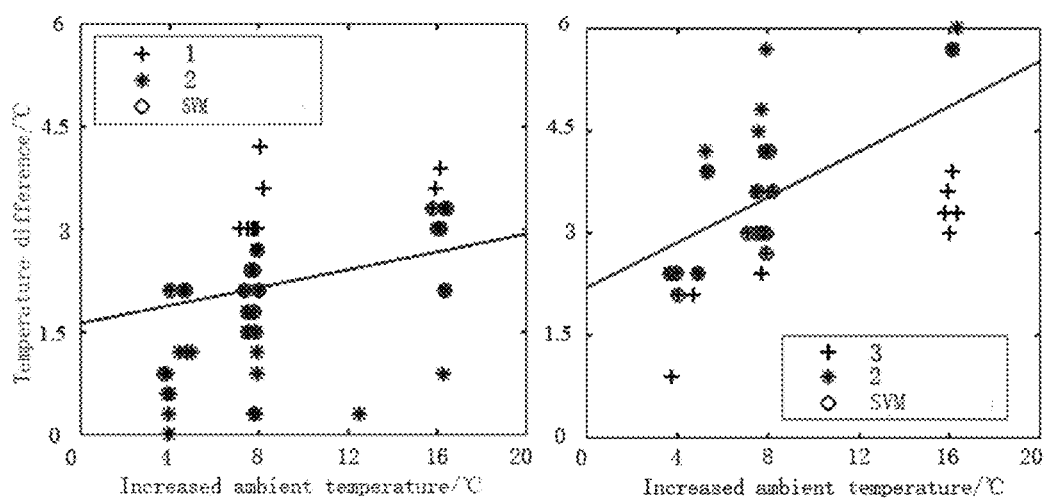
FIG. 11 is a linear classification diagram of the support vector machine.
Figure 12:
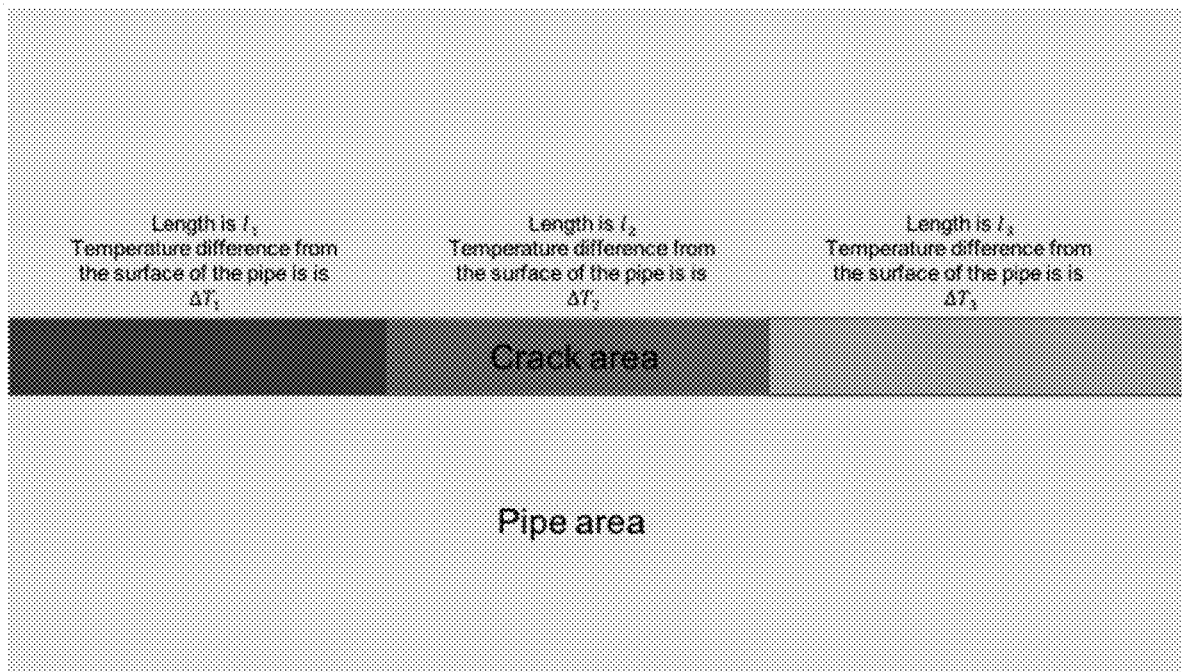
FIG. 12 is a schematic diagram showing different temperature differences obtained for different crack sections.

Degree of development referred to the extent of damage to the pipeline caused by the leaking cracks and the severity of recent damages. It covers the conventional classification of crack severity. The length, width, and area of the crack may increase the severity of crack damage, which characterize the level of development of cracks from the beginning to the present.

SVM (support vector machine) is a machine learning method based on statistical learning theory developed in the mid-1990s. It seeks to maximize the learning machine's generalization ability by minimizing the structural risk and minimize the empirical risk and confidence range. In the case of a small amount of statistical samples, the purpose of good statistical laws can also be obtained. In machine learning, support vector machines (SVMs, which also support vector networks) are supervised learning models that can analyze data, identify patterns, and use for classification and regression analysis. Given a set of training samples, an SVM training algorithm builds a model, assigning new instances to one class or other classes, making it a non-probabilistic binary linear classification. Generally speaking, it is a two-class classification model. The basic model is defined as the linear classifier with the largest interval in the feature space. That is, the learning strategy of the support vector machine is to maximize the interval, which is finally transformed into solving a convex quadratic programming problem.

Classification function: through the support vector machine, the temperature difference data is linearly classified according to the degree of crack development. The development degree is divided into three levels of 1, 2, and 3, and the most serious is 3. There will be a straight line between 1, 2 and 2, 3 as a dividing line, and this line expression is the classification function.

Fracture zone: a certain area of the pipeline, which includes not only the crack area itself, but also a certain area of the pipeline area around it, including the pipeline area, which meets the requirements of image processing and crack identification.

Reference temperature difference data obtained by plugging the measured ambient temperature into the two classification functions of the crack development degree detection model.

Measured temperature difference data: the temperature difference data of the crack region and the pipeline surface region in fracture zone obtained by infrared images.

Degree of distortion is the deviation between the unreasonable value and the reasonable value after the data generates an unreasonable value.

Developmental level: a number of 1, 2 or 3 which reflects the degree of development of the crack. The larger the number, the more serious the crack development.

Developmental index: between 0-3, including a number of 0 and 3, its size reflects the degree of development of the crack, the greater the number, the more serious the degree of crack development. The description is indicated by the letter m.

Leakage severity index means the average degree of severity of pipe cracks in three dimensions of length, width, and area. The value range is between [0-9.9], and 1 decimal place is reserved. The size reflects the severity of the leak. The larger the number, the more serious the leak.

(1) Environmental Determination

The test model needs to be used under certain environmental conditions to ensure accuracy. Firstly, it is necessary to ensure that the environmental conditions during data collection are met: the dark and humid underground pipeline corridor space, and the ambient temperature in the pipeline corridor space rises evenly above 4° C. It is necessary to ensure that the environmental conditions are stable when the data is collected, that is, the ambient temperature inside the pipeline corridor is uniform, and after a certain temperature is raised, no drastic changes will occur.

(2) Image Acquisition

The inner space of the pipeline corridor is photographed by a temperature-measuring infrared thermal imaging camera, and the infrared thermal image video of the crack region is analyzed. Based on the Matlab program, a frame image is extracted from the video collected by the mobile inspection device. The thermal imager shoots a horizontal distance of 1 m from the pipeline, and the machine position is kept at a constant speed from the crack area. The infrared camera uses an infrared detector and an optical imaging objective to receive the infrared radiation energy distribution pattern of the target. It can be reflected on the photosensitive element of the infrared detector, thereby obtaining an infrared thermal image. The thermal image corresponds to the heat distribution field on the surface of the object. In general, an infrared camera converts invisible infrared energy emitted by an object into a visible thermal image. The different colors above the thermal image represent the different temperatures of the object being measured. Invention of the current mainstream infrared imaging device is uncooled focal plane infrared detector. At the same time, it is necessary to record the temperature and crack developmental degree when collecting crack images. The ambient temperature is directly measured by a thermometer, and the crack developmental degree is manually measured according to the crack width.

At the same time, it is necessary to score the true developmental index of the crack, mainly referring to the traditional classification method, that is, the crack is divided into three categories of light, medium and heavy, and then the factors such as the humidity and depth of the crack are considered. The developmental degree index is scored by the experts, and the detection model is established based on the actual data.

(3) Image Analysis

Firstly, image preprocessing is performed to grayscale the infrared image; wavelet denoising and median filtering processing of different rectangles are used for the image (when filtering noise, try not to blur the edge); image gray enhancement algorithm is used to enhance the contrast between the crack and the background area facilitates; the image segmentation algorithm with an adjustable threshold is used to segment the image, the crack region and the impurity with lower gray value are converted to black, and the background with higher gray value is converted to white; the impurity and the non-crack area can be removed by the area threshold and the area-circumference fractal rule, with only the crack area is retained. Then, the crack area and the non-crack area of the pipeline surface are obtained; the area positioning is performed in the initial infrared image according to the two kinds of position; finally, the RGB average value of the infrared image crack area and the pipeline surface area is calculated, and the RGB average value is sequentially followed by the colorbar legend. The temperature represented by the most consistent position is the temperature of the region. The crack region and the pipe surface region are respectively matched with the legend to obtain respective temperatures, thereby obtaining the temperature difference between the crack and the pipe surface.

The image segmentation technology in image processing can identify the crack area directly after the temperature identification process of the crack area and the pipe surface area, and can also analyze the transition interference zone directly between the crack and the pipe surface according to the foregoing.

The final temperature difference data can be obtained directly to calculate the temperature difference between the entire crack area and the surface area of the pipeline. It is also possible to divide the crack area into sections, and the average distribution method can be adopted, and then the section with higher developmental index is given. The high weight is calculated according to the method of giving different weights to calculate the temperature difference between the final crack area and the surface area of the pipeline.

(4) Model Establishment

Considering the different conditions of different pipeline corridor environments, it is possible to try to establish a model of the relationship between the temperature difference of cracks and the ambient temperature conditions in the pipeline corridor environment of the region. According to the historical data, the current data is corrected and discarded; the temperature difference obtained by image analysis, and the temperature information collected by other instruments and the temperature difference data collected by the optical fiber temperature measurement are used to correct the relationship model. After the above three steps, we have data on the difference between crack and pipe surface temperature, the degree of development, and the ambient temperature data when each sample is collected. The temperature difference obtained by image analysis and the acquired image are collected by other instruments. The temperature information is established to be related to the degree of development, that is, the specific value of the correlation coefficient that mainly determines the linear classification function $l_{12}$ and $l_{23}$.

(5) Test Verification

The above detection model can be used to detect the actual degree of development of crack, and it is necessary to collect the infrared image of the cracked pipeline surface and the current ambient temperature.

When calculating the developmental degree of crack, the index can be roughly divided into three levels of 1, 2, and 3, and only one of the three numbers can be taken. The larger the value, the more serious the degree of development will be. The calculation can also use the developmental index with a decimal number as mentioned above, the value range is 0-3, and the specific development degree index can be expressed as $m \pm a\sigma$.

The above is only exemplary embodiments of the present invention, but the scope of the present invention is not limited thereto. Any changes or substitutions that can be easily thought by those skilled in the art within the technical scope of the present invention, should fall within the scope of the present invention. Therefore, the scope of the present invention should be determined by the appended claims.

What is claimed is:

1. A method for leakage detection of underground pipeline corridor based on dynamic infrared thermal image processing, comprising:

a) establishing a crack development degree detection model, comprising:

a1) collecting infrared thermal images of at least ten crack samples on pipe surface of the underground pipeline corridor; recording a sample ambient temperature and a crack development degree; and estimating and ranking the crack development degree into three developmental levels: 1, 2, and 3;

a2) processing the infrared thermal images, obtaining the reference temperature difference data between the crack samples and the pipe surface; and a3) based on the reference temperature difference data, the ambient temperature and the crack development degree, obtaining two classification functions with SVM classification: $\Delta T_{12}=a_{12}T+b_{12}$ and $\Delta T_{23}=a_{23}T+b_{23}$, wherein T is the ambient temperature, and $\Delta T$ is the reference temperature difference data;

b) data collecting: collecting infrared thermal videos of the fracture zone of underground pipeline corridor, and recording the ambient temperature;

c) data pre-processing: converting the infrared thermal videos into the infrared thermal images, along with image denoising and grayscale conversion of the collected infrared thermal images;

d) data processing: processing denoised and grayscale infrared thermal images, including edge detection and image enhancement, edge extraction, impurity removal, and calculating measured temperature difference data;

e) temperature difference data processing: comprising distortion degree judgment, first correction of the measured temperature difference data, and second correction of the measured temperature difference data; and f) leakage analysis: comprising calculating the reference temperature difference data, and determining leakage severity, and determining type of leakage.

2. The method of claim 1, wherein step b) comprises:

b1) collecting with mobile patrol equipment: using an infrared imaging device-uncooled focal plane infrared detector, which is placed on the mobile patrol equipment, to inspect the fracture zone regularly, a height of the equipment from the surface of the pipe is 0.5-1 m; collecting the infrared videos of fracture zone of underground pipeline corridor; and b2) recording the ambient temperature: using a thermometer in the fracture zone of the underground pipeline corridor and recording the ambient temperature.

3. The method of claim 1, wherein step c) comprises:

c1) videos conversion to images: converting the infrared thermal videos into the infrared thermal images by frame-by-frame extraction;

c2) image denoising: denoising of the infrared thermal images, and reducing noise interference generated in transmission or in digital processing; and c3) grayscale conversion: converting the originally collected color image into a grayscale image, by removing the color information in the image.

4. The method of claim 3, wherein the image denoising in step c2) is performed by one or more of mean filter, adaptive Wiener filter, median filter, morphological noise filter, and wavelet denoising.

5. The method of claim 1, wherein step d) comprises:

d1) edge detection and image enhancement: using search and zero-crossing to identify significant changes in image properties, and to extract temperature difference points;

d2) edge extraction: locating crack area and non-crack area, using single threshold segmentation method or multi-threshold segmentation method;

d3) impurity removal: removing impurities and non-crack area, obtaining effective pipeline region and the effective crack region; and d4) calculating the measured temperature difference data: processing the infrared thermal images of the effective pipe surface region and the effective crack region, and obtaining the measured temperature difference data $\Delta T$.

6. The method of claim 5, wherein an edge detection template used in step d1) is at least one of Laplacian operator, Roberts operator, Sobel operator, log (Laplacian-Gauss) operator, Kirsch operator and Prewitt operator.

7. The method of claim 5, wherein step d4) comprises:

d41) matching the effective pipeline region with legend, and obtaining measured temperature $T_0$;

d42) dividing the crack region into p segments, p≥2; a length of each segment is $l_1, l_2, \ldots l_p$; matching each segment with the legend, and obtaining measured temperature $T_1, T_2, \ldots T_p$, respectively;

d43) obtaining measured temperature differences $\Delta T_1, \Delta T_2, \ldots \Delta T_p$; and d44) calculating measured temperature difference data $\Delta T$:

$$\Delta T=(T_1 l_1+T_2 l_2+ \ldots +T_p l_p)/(l_1+l_2+ \ldots +l_p).$$

8. The method of claim 1, wherein step e) comprises:

e1) distortion degree judgment: comparing measured temperature difference data with the historical period data according to three characteristics of irreversibility, continuity and trend;

e2) first correction of the measured temperature difference data: selecting and correcting the measured temperature difference data with distortion according to the historical measured temperature difference data and the three characteristics of leakage, to obtain a corrected measured temperature difference data; and e3) second correction of the measured temperature difference data: selecting and correcting the measured temperature difference data after the first correction, according to the temperature difference data collected by the optical fiber temperature measurement; replacing the original temperature difference data by the fiber temperature measurement data if the fiber temperature measurement data is available to obtain the measured temperature difference data after the second correction.

9. The method of claim 1, wherein step f) comprises:

f1) calculating the reference temperature difference data: calculating the reference temperature difference data based on the crack development degree detection model; the reference temperature difference data and the second corrected measured temperature difference data are brought into the step a) of detection model to estimate the degree of crack development;

f2) determining leakage severity: defining the severity of the leakage from the three dimensions of length, width and area, and obtaining G=[0-9.9], wherein G is the leakage severity index, and the result retains 1 decimal place; and f3) determining type of leakage: discriminating the characteristics of the fracture zone based on the method of regional feature analysis, considering the roundness and density parameters, and judging the leakage type of the leakage point of the pipeline crack zone.

10. The method of claim 9, wherein the method of determining the type of leakage comprises:

f31) if a perimeter/area of a leaking area is >0.5, the leak is considered to be a crack;

f32) if the perimeter/area of a leaking area is not >0.5, and if $S_1/S_2>3.18$, the leak is considered to be loose-like leakage of the interface;

f33) if the perimeter/area of a leaking area is not >0.5, and if $1<S_1/S_2<3.18$, the leak is considered to be other types of leakage;

wherein in the step f32) and f33), $S_1$ is the area of the circumscribed rectangle of the leaking region, and S: is the area of the region.

* * * * *